United States Patent
Yeh (10) Patent No.: US 10,166,108 B2
(45) Date of Patent: Jan. 1, 2019

(54) BUFFERABLE FEMORAL IMPLANT

(71) Applicant: Paonan Biotech Co., Ltd., Taipei (TW)

(72) Inventor: Chung-Chun Yeh, Taipei (TW)

(73) Assignee: Paonan Biotech Co., Ltd., Taipei (TW)

( * ) Notice: Subject to any disclaimer, the term of this patent is extended or adjusted under 35 U.S.C. 154(b) by 183 days.

(21) Appl. No.: 15/099,839

(22) Filed: Apr. 15, 2016

(65) Prior Publication Data

US 2016/0310281 A1  Oct. 27, 2016

(30) Foreign Application Priority Data

Apr. 21, 2015 (TW) .............................. 104112818 A (51) Int. Cl.
*A61F 2/36* (2006.01)
*A61F 2/30* (2006.01)
*A61F 2/46* (2006.01)

(52) U.S. Cl.
CPC ............ *A61F 2/3672* (2013.01); *A61F 2/367* (2013.01); *A61F 2/3662* (2013.01); *A61F 2/3676* (2013.01); *A61F 2002/30069* (2013.01); *A61F 2002/30341* (2013.01); *A61F 2002/30433* (2013.01); *A61F 2002/30822* (2013.01); *A61F 2002/30828* (2013.01); *A61F 2002/30831* (2013.01); *A61F 2002/30909* (2013.01); *A61F 2002/368* (2013.01); *A61F 2002/3668* (2013.01); *A61F 2002/3674* (2013.01); *A61F 2002/3694* (2013.01); *A61F 2002/4631* (2013.01); *A61F 2250/0024* (2013.01); *A61F 2310/00011* (2013.01)

(58) Field of Classification Search
CPC .................. A61F 2/3672; A61F 2/3676; A61F 2002/3052; A61F 2002/3635; A61F 2002/3674
See application file for complete search history.

(56) References Cited

U.S. PATENT DOCUMENTS

| | | | | |
|---|---|---|---|---|
| 3,938,198 | A * | 2/1976 | Kahn .................. | A61F 2/30907 623/22.15 |
| 4,619,659 | A * | 10/1986 | Witzel ................ | A61F 2/30907 623/23.36 |
| 4,784,124 | A * | 11/1988 | Kaltenbrunner ..... | A61B 17/164 606/63 |
| 4,892,550 | A * | 1/1990 | Huebsch ............ | A61B 17/8822 623/23.19 |
| 4,892,551 | A * | 1/1990 | Haber ................ | A61F 2/32 623/23.17 |
| 5,116,377 | A * | 5/1992 | Skripitz .............. | A61F 2/30728 623/23.19 |

(Continued)

FOREIGN PATENT DOCUMENTS

WO  WO 2006114091 A1 *  11/2006  ........... A61F 2/3662

*Primary Examiner* — Thomas J Sweet
*Assistant Examiner* — Megan Wolf
(74) *Attorney, Agent, or Firm* — Wang Law Firm, Inc.

(57) ABSTRACT

A bufferable femoral implant includes a metallic main body, and an elastomer member integrally formed or connected to a lower portion of the metallic main body, whereby when an external force acts upon the femoral implant as implanted in a patient's femur, the elastomer member as packed within the medullary cavity in the femur will bufferably dampen such an external force for safely protecting the patient's femur, the femoral implant and the related hip bones.

8 Claims, 12 Drawing Sheets

(56) References Cited

U.S. PATENT DOCUMENTS

| | | | | |
|---|---|---|---|---|
| 5,176,712 A | * | 1/1993 | Homsy | A61F 2/30734 |
| | | | | 623/23.36 |
| 5,197,988 A | * | 3/1993 | Spotorno | A61F 2/367 |
| | | | | 623/23.28 |
| 5,397,359 A | * | 3/1995 | Mittelmeier | A61C 8/0012 |
| | | | | 623/1.5 |
| 5,653,765 A | * | 8/1997 | McTighe | A61F 2/36 |
| | | | | 623/18.11 |
| 5,954,771 A | * | 9/1999 | Richelsoph | A61F 2/30723 |
| | | | | 623/23.15 |
| 6,162,255 A | * | 12/2000 | Oyola | A61F 2/389 |
| | | | | 623/20.15 |
| 7,220,283 B2 | * | 5/2007 | Terrill | A61F 2/3609 |
| | | | | 623/22.44 |

* cited by examiner

BUFFERABLE FEMORAL IMPLANT

RELATED APPLICATION

This application claims the benefit of a Taiwanese patent application, 104112818, filed on Apr. 21, 2015, the specification of which is incorporated here by this reference.

BACKGROUND OF THE INVENTION

In a hip joint replacement surgery, an artificial femoral prosthesis is implanted into a patient's femur for completing the surgery.

Figure 1:
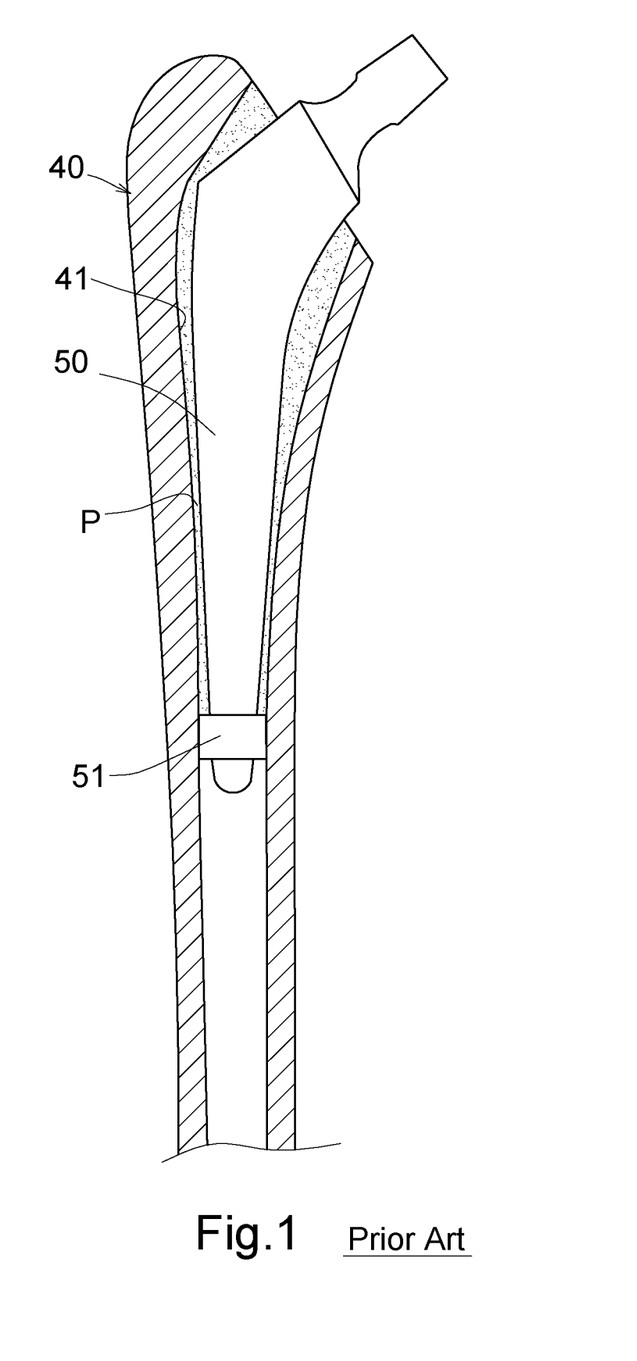
FIG. 1 shows a prior art of a femoral stem implanted in a medullery cavity of a femur.

A conventional femoral stem 50 as shown in FIG. 1 is provided or served for such an artificial femoral prosthesis. The femoral stem 50 is integrally formed by metallic materials and is tapered downwardly adapted to be inserted into a medullary cavity 41 in a patient's femur 40. A centering retainer 51 is jacketed on a bottom tip of the femoral stem 50. Before inserting the femoral stem 50 into the medullary cavity 41 of the femur 40, a fixation agent P such as bone cement is filled into the medullary cavity 41. Upon insertion of the femoral stem 50 into the medullary cavity 41, the femoral stem 50 will be suspended within the fixation agent P. By the aid of centering retainer 51, the stem 50 will then be automatically positioned in the central position of the medullary cavity 41. After the fixation agent P is cured, the femoral stem 50 will be stably implanted in the medullary cavity 41 of the femur 40.

Figure 2:
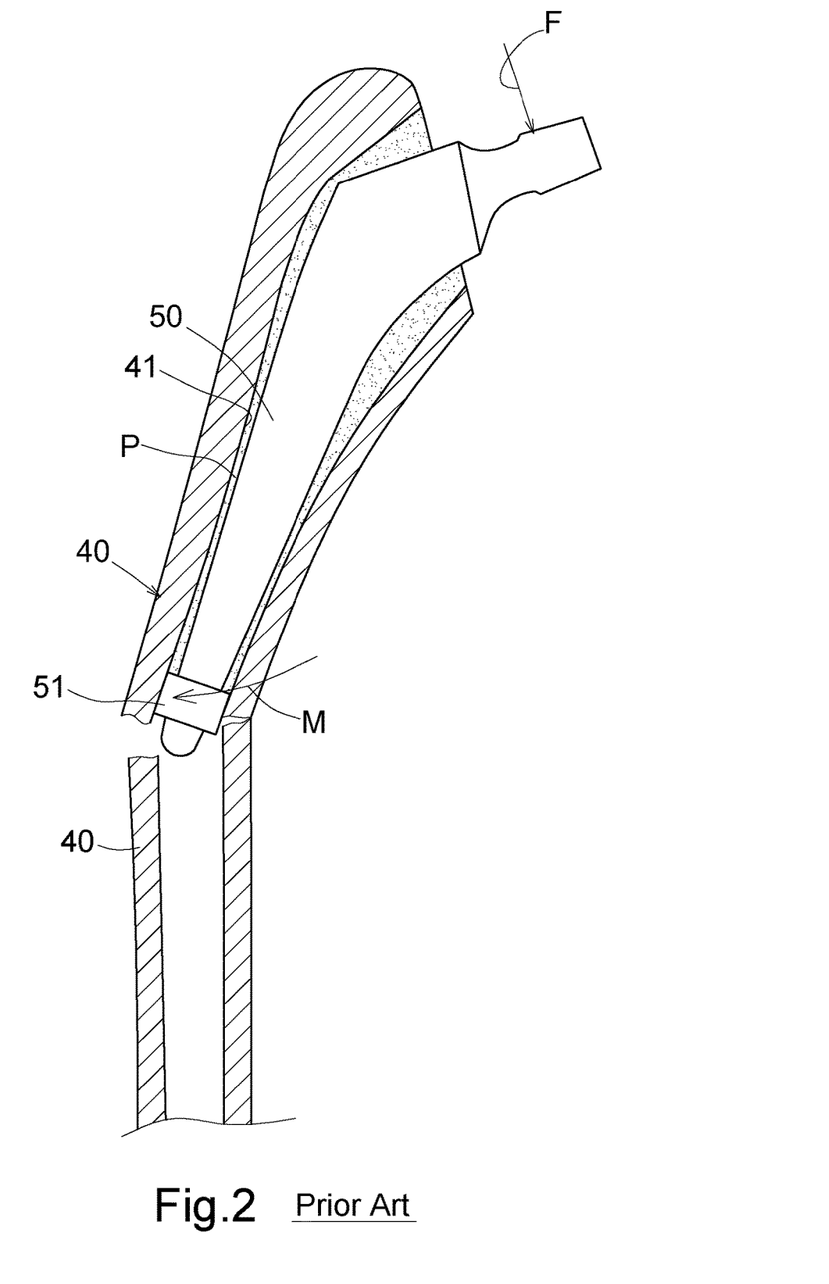
FIG. 2 is an illustration of the prior art of FIG. 1, showing a fractured femur when impacted by an external force.

After the fixation agent P is cured, the hardened fixation agent P will lose its buffer effect. So, any external impact force acting upon the femoral stem 50 will be directly transferred to the femur 40, without being diffused or dampened. As shown in FIG. 2, if the external force F acts on the top portion of the stem 50, a bending moment M will exert on the stem 50 to thereby bias the femur 40 to possibly cause fracture of the femur 40 or stem 50, resulting in a failure of the hip joint replacement surgery.

It is therefore expected to design or create a femoral implant having a buffer mechanism provided therein so as to dampen any external force acting thereupon for a safe protection of the femoral implant and femur.

SUMMARY OF THE INVENTION

The object of the present invention is to provide a bufferable femoral implant including a metallic main body, and an elastomer member integrally formed or connected to a lower portion of the metallic main body, whereby when an external force acts upon the femoral implant as implanted in a patient's femur, the elastomer member as packed within the medullary cavity in the femur will bufferably dampen such an external force for safely protecting the patient's femur, the femoral implant and the related hip bones.

DETAILED DESCRIPTION

As shown in FIGS. 3, 4, 9 and 13, the femoral implant of the present invention comprises: a femoral stem 100, which includes: a metal main body 10 made of titanium alloy, stainless steel and other suitable materials; a coupling rod 20; and an elastomer member 30.

The metal main body 10 includes: a plug member 11 adapted to be inserted into a medullary cavity 41 of a patient's femur 40, and an artificial femoral neck 111 formed on a top portion of the plug member 11 and connected with an artificial femoral head 112 adapted to be coupled to acetabulum or cup of a patient's hip bone.

The lower portion of the plug member 11 is downwardly longitudinally or axially coupled, connected or formed with the coupling rod 20.

The elastomer member 30 may be integrally formed (not shown) with a lower or bottom portion of the metal main body 10. However, the elastomer member 30 is preferably connected or coupled to the metal main body 10 by the aid of the coupling rod 20 for a more stable and stronger connection or coupling of the main body 10 and the elastomer member 30.

The elastomer member 30 is made of biocompatible elastomer materials including polyurethane and other suitable elastomeric polymers, composites or materials, not limited in the present invention.

The elastomer member 30 may have a longitudinal or axial length which is larger than 3 centimeters, and includes a rod hole 31 longitudinally formed through the elastomer member 30 adapted for passing or inserting the coupling rod 20 through the rod hole 31. The longitudinal length of the elastomer member 30, as being larger than 3 cm, is provided to render an enough contacting area between the elastomer member 30 and an inner wall of the medullary cavity 41.

For instance, a pressure forcing the inner wall of the medullary cavity 41 is set as "p", and the stress as formed by the external force F acting upon the femoral implant of the present invention is indicated as S, the pressure "p" may be obtained in accordance with the following simple formula:

$$p = S/A$$

wherein, the numeral A, indicating the contacting area between the elastomer member 30 and the inner wall of the medullary cavity 41, should be large enough (corresponding to the enough length of the elastomer member 30) in order to reduce or minimize the pressure "p" as effected by the stress S due to external force F acting on the femoral implant of the present invention, thereby dampening or buffering the external force so as for effectively protecting the femur 40. If "A" is too small (means that the elastomer member 30 is too short), the "p" will be increased to possibly affect the wall of the medullary cavity of the femur 40.

Figure 10:
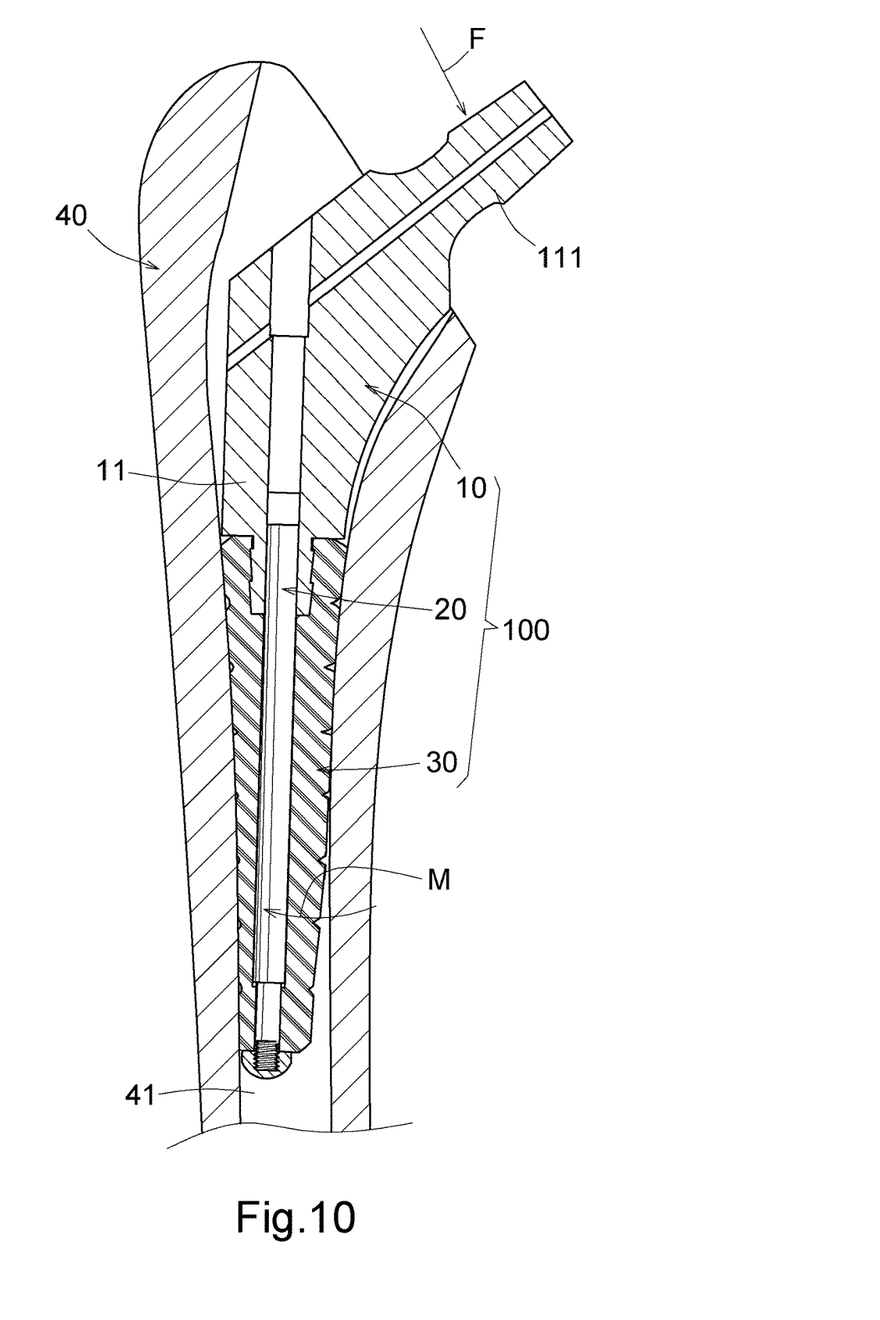
FIG. 10 is an illustration of the present invention, showing the femoral implant resiliently compressed and biased when attacked by an external force.

This can be clearly illustrated in FIG. 10, in which an external force F acting on the upper portion of the femoral implant of the present invention will produce a biasing stress acting upon the inner wall of the medullary cavity 41 of the femur 40, indicated as numeral M. Nevertheless, such a laterally acting biasing stress or moment acting on the cavity wall of the femur 40 will be dampened or buffered since the elastomer member 30 is resilient, elastomeric, compressible, squeezable or expansible so as to dampen or reduce or even eliminate the biasing moment or stress (M), as derived from the external force F, acting upon the femur 40 or the femoral stem 100 of the present invention, thereby preventing fracture of the patient femur, hip bone joint and efficiently protecting the femoral implant, the femur and hip bone accordingly.

Figure 3:
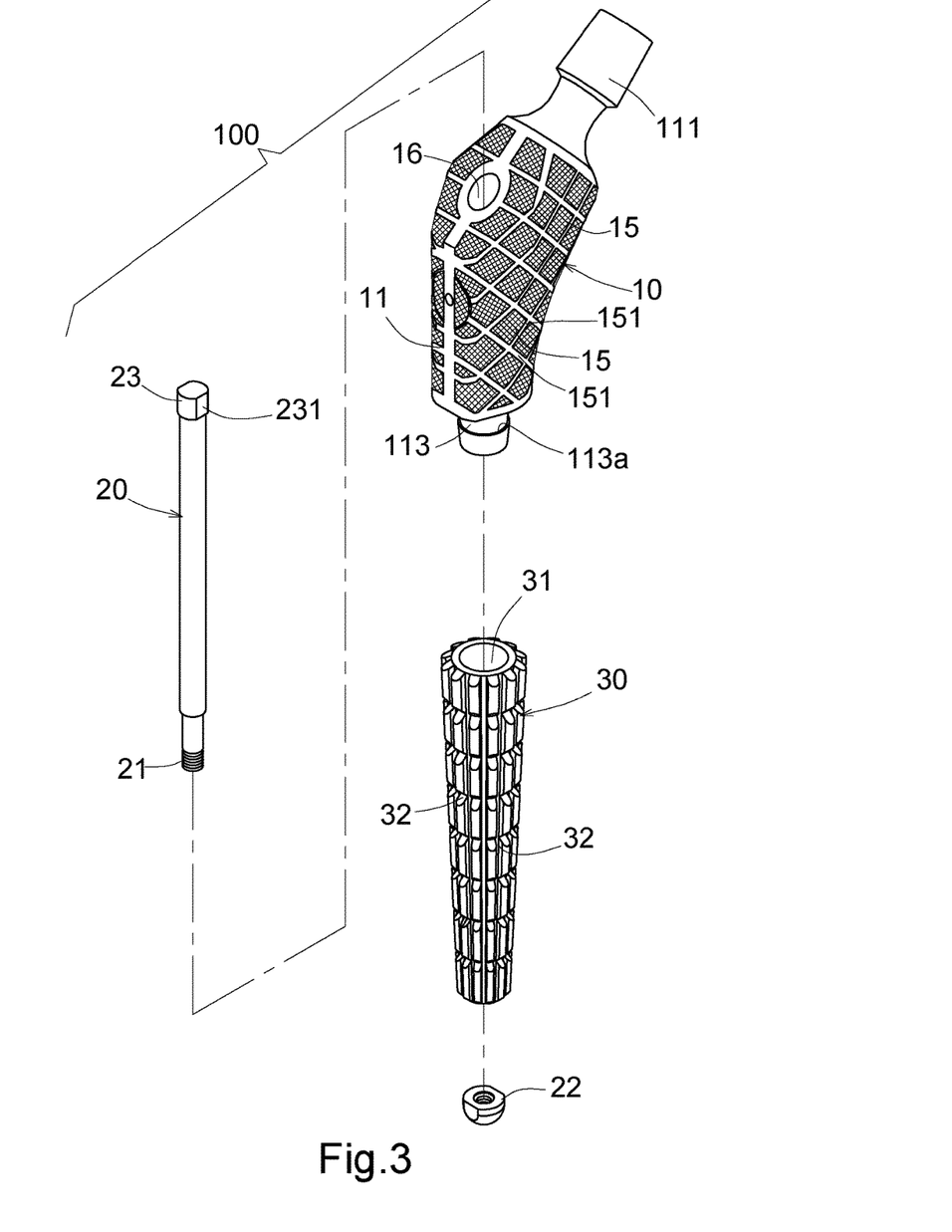
FIG. 3 is a perspective exploded view of the present invention.
Figure 4:
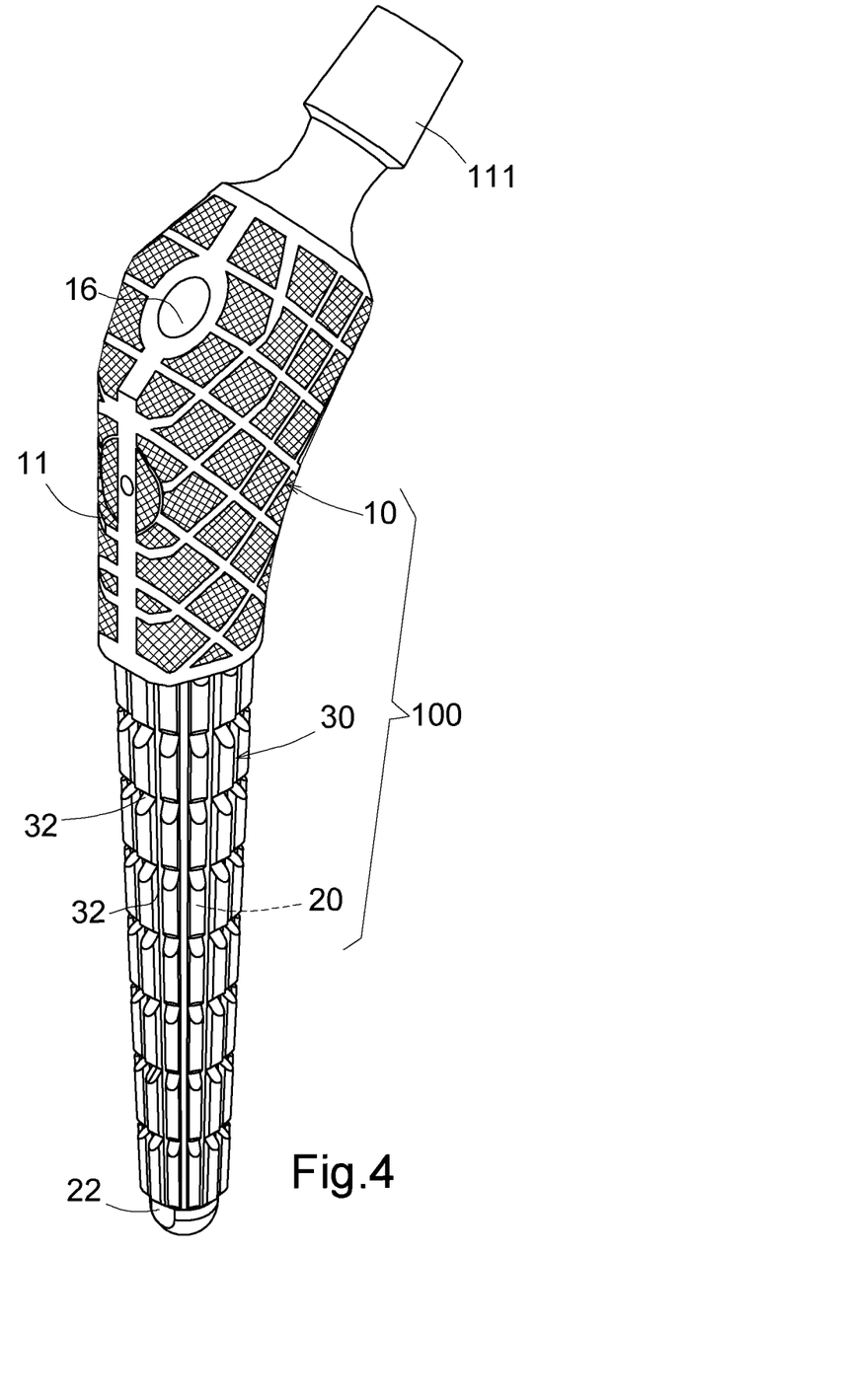
FIG. 4 is a perspective view of the present invention when assembled.

As shown in FIGS. 3 and 4, the main body 10 further includes a three-dimensional mesh grid 15 having a plurality of pores or microspores formed in the mesh grid 15. Also, the main body 10 includes a plurality of fusion ribs 151 interlaced or circumferentially formed on an outer surface of the main body 10 for defining a plurality of fusion lattices. By the way, the bone tissue will re-grow into or onto the pores or fusion lattices as defined by the fusion ribs 151 of the three-dimensional mesh grid 15 for regenerating a strong femur reinforced with the femoral stem 100. Each pore may have on opening size ranging from 200 through 650 microns.

Figure 9:
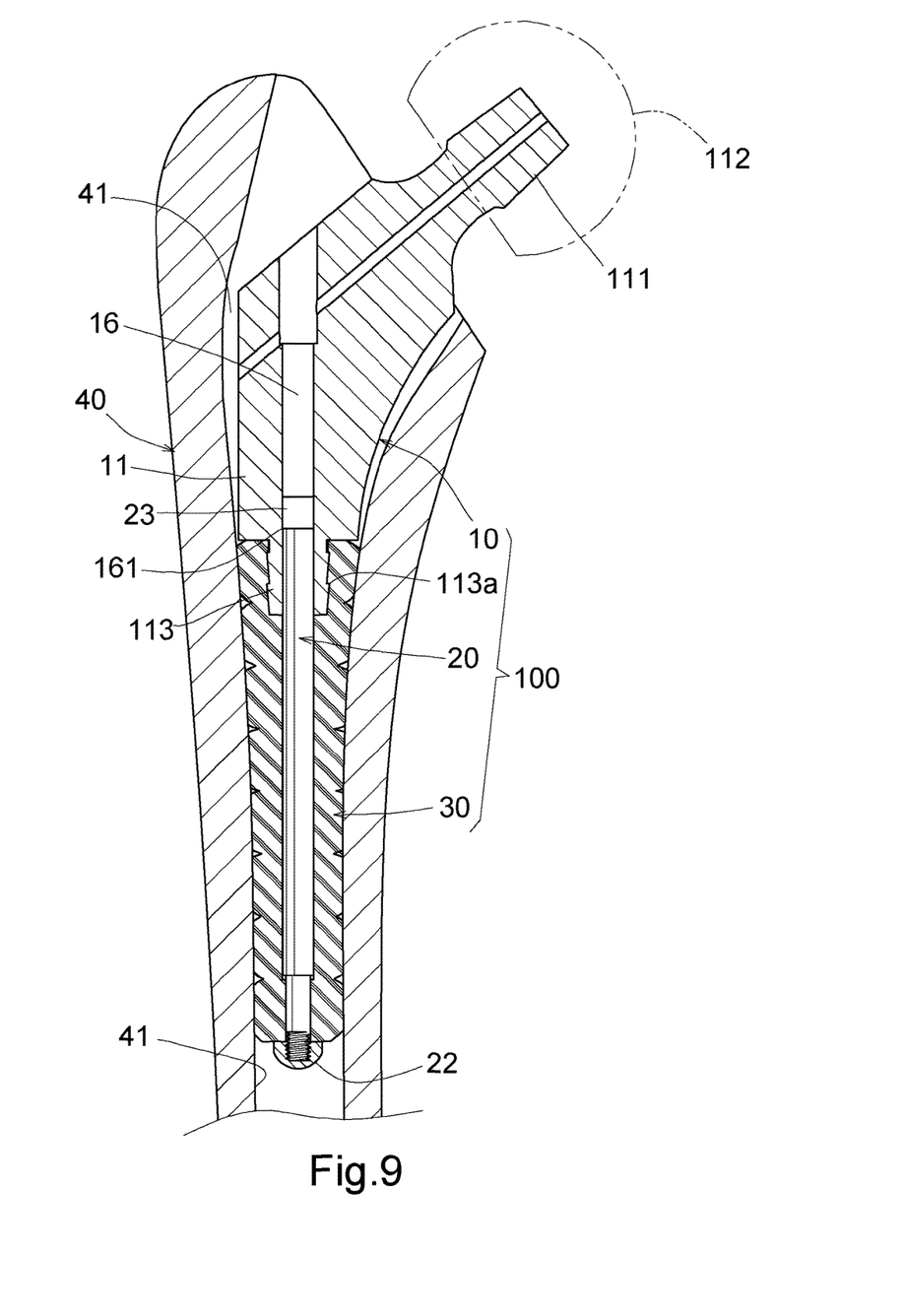
FIG. 9 is a partial sectional drawing of the present invention when mounting the femoral implant into a femur.

As shown in FIGS. 3, 4 and 9, the coupling rod 20 is formed with a lower threaded rod portion 21, which can be fastened by a retainer or nut 22 for firmly fastening the elastomer member 30 with the plug member 11 of the main body 10 as locked or limited by the retainer 22 after inserting the coupling rod 20 through the rod hole 31 in the elastomer member 30. The retainer 22 has an outside diameter larger than the opening size of the rod hole 31 for preventing the releasing or removal of the elastomer member 30 from the coupling rod 20 or the main body 10. The retainer 22 may be further modified to be integrally securable to the bottom of the coupling rod 20 to prevent from its loss.

Figure 5:
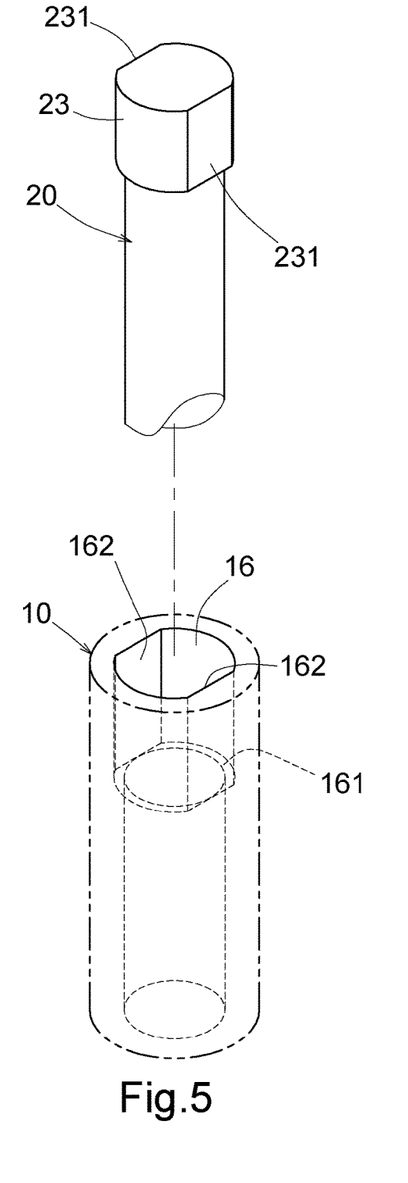
FIG. 5 is an exploded view showing the fixing head of the coupling rod adapted to be coupled with the rod-penetrating hole ins the metal main body of the present invention.
Figure 6:
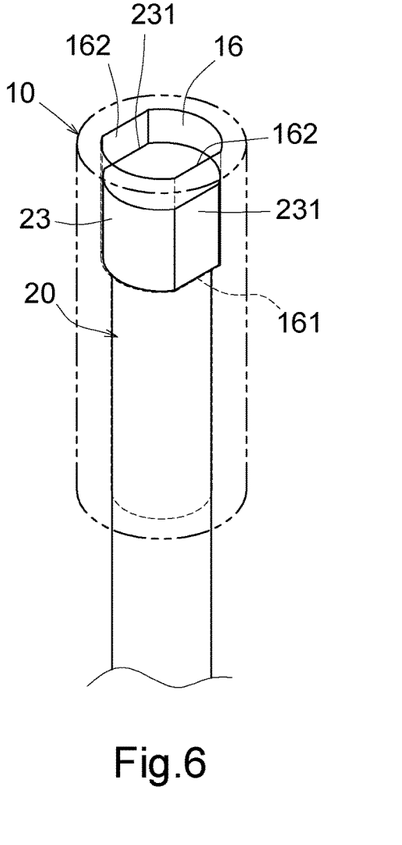
FIG. 6 shows the fixing head coupled with the rod-penetrating hole as assembled from FIG. 5.

As shown in FIGS. 3, 5 and 6, the main body 10 of the femoral stem 100 of the present invention is formed with a rod-penetrating hole 16 in the main body 10 for inserting the coupling rod 20 through the rod-penetrating hole 16, whereby after the coupling rod 20 is inserted through the rod hole 31 of the elastomer member 30, the retainer 22 is served to lock or limit the elastomer member 30 with the coupling rod 20 to thereby stably mount the elastomer member 30 with the coupling rod 20 and with the plug member 11 of the main body 10. A fixing head 23, as formed on a top portion of the rod 20, is longitudinally formed with a retarding secant surface 231, and the rod-penetrating hole 16 is formed with an anti-rotation secant wall 162 on a secant surface of the rod-penetrating hole 16 so as to engage the retarding secant surface 231 of the fixing head 23 with the anti-rotation secant wall 162 of the rod-penetrating hole 16 for preventing rotation of the coupling rod 20 within the hole 16. The rod-penetrating hole 16 is formed with a retarding shoulder portion 161 as slightly recessed in the hole 16 at a lower portion of the plug member 11 in order to limit a downward movement of the head 23 of the coupling rod 20 when the rod 20 is inserted through the hole 31 in the elastomer member 30. Upon being fastened by the retainer 22, the rod 20 and the elastomer member 30 will be stably coupled to the plug member 11 of the main body 10 of the femoral stem 100 of the present invention.

Figure 12:
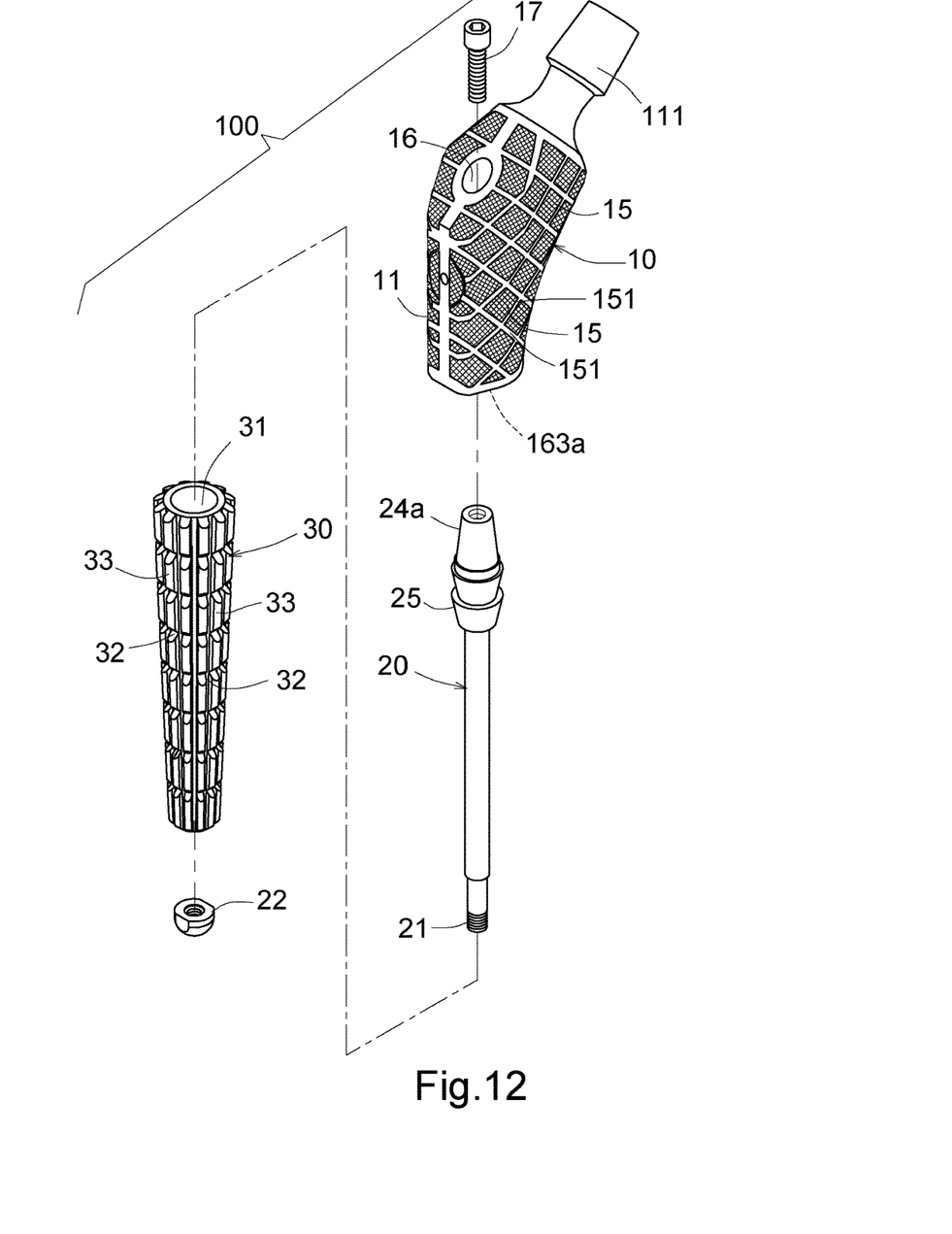
FIG. 12 shows another preferred embodiment of the present invention.
Figure 13:
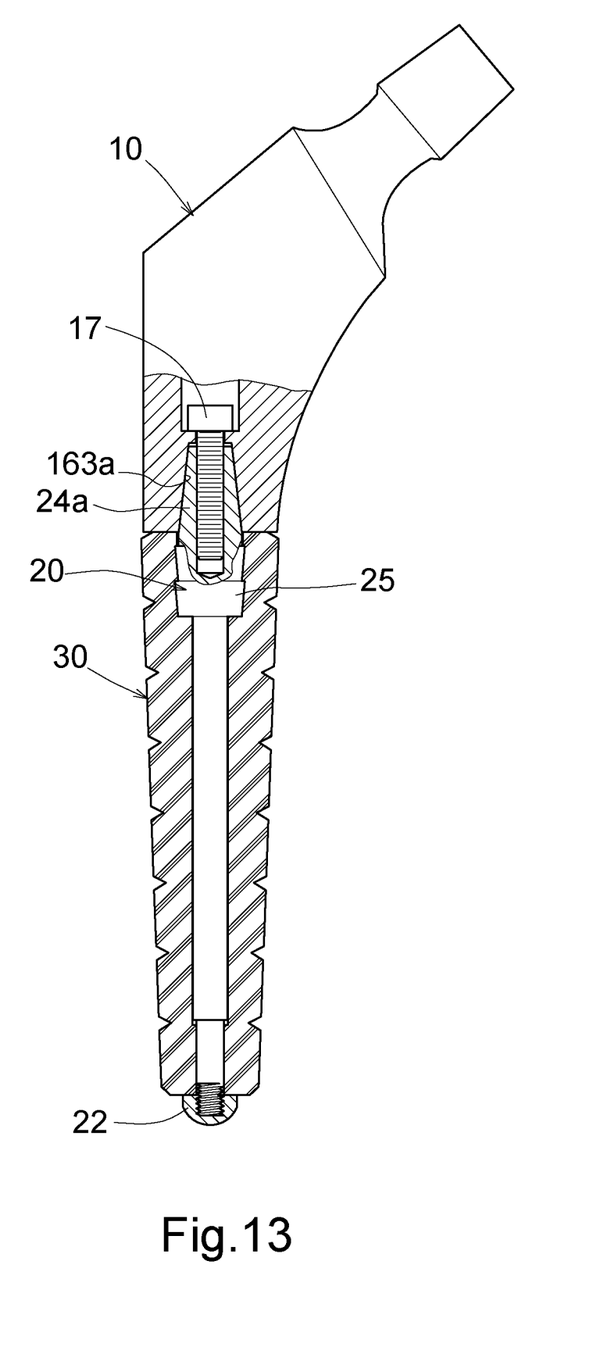
FIG. 13 is a sectional drawing when the embodiment of FIG. 12 is assembled.

As shown in FIGS. 3 and 9, the plug member 11 is formed with an adaptor 113 having a plurality of ratchet rings 113a circumferentially formed on the adaptor 113 for firmly coupling or fastening an upper portion of the elastomer member 30. Alternatively, the coupling rod 20 may be formed with a coupling head 24a tapered upwardly on a top portion of the coupling rod 20 to be engaged with a receiving socket 163a tapered upwardly in a bottom portion of the plug member 11 and a fixing screw 17, which may be screwed into the coupling head 24a, is provided for fastening the coupling head 24a of the coupling rod 20 with the plug member 11 of the main body 10 as shown in FIGS. 12 and 13.

Figure 7:
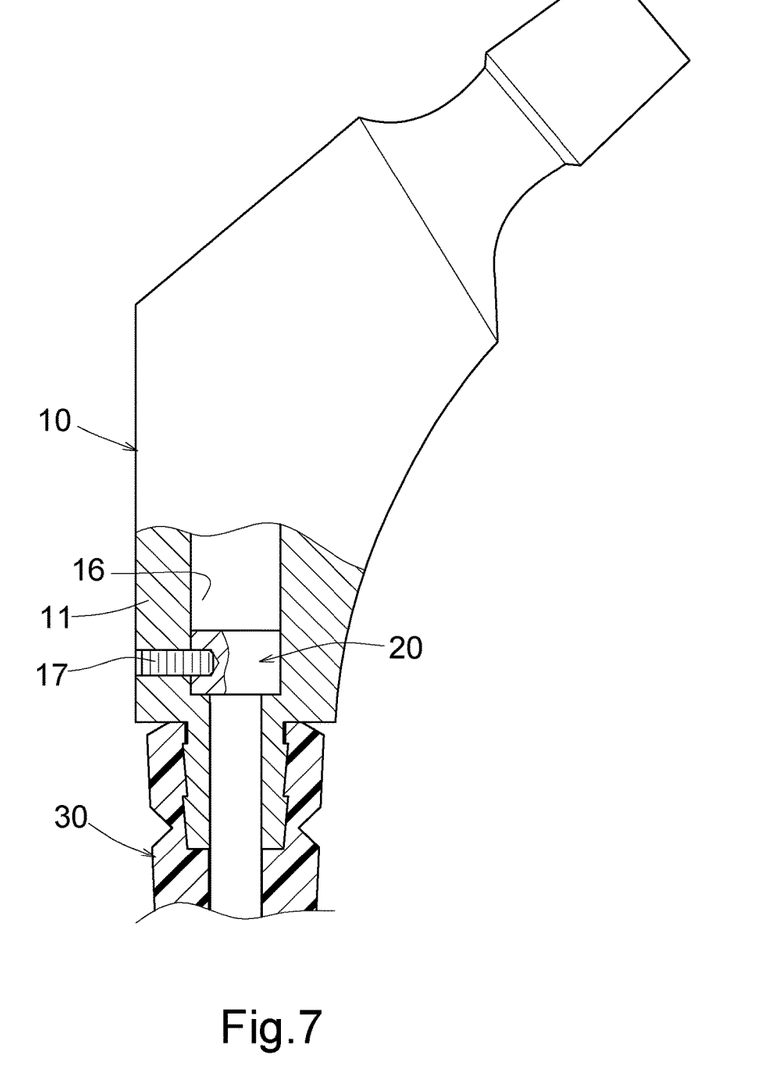
FIG. 7 shows a second assembly method for coupling the main body with the coupling rod in accordance with the present invention.
Figure 8:
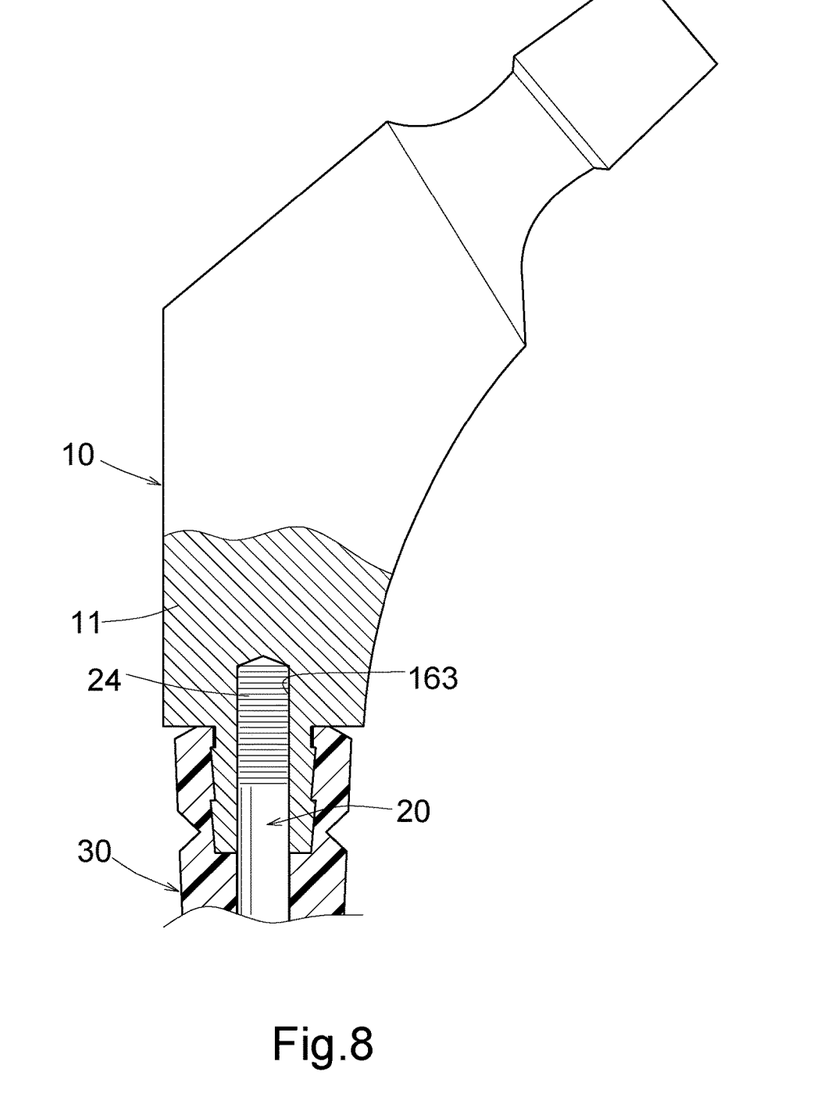
FIG. 8 shows a third assembly method for coupling the main body with the coupling rod in accordance with the present invention.

As shown in FIG. 7, a fixing screw 17 is provided to transversely or radically fasten the coupling rod 20 with the plug member 11 for fastening the coupling rod 20 with the plug member 11. Alternatively, the coupling rod 20 may be formed with a threaded portion 24 in order to be fastened with a female-threaded hole 163 formed in a lower portion of the plug member 11 so as to firmly fasten the coupling rod 20 with the main body 10 as shown in FIG. 8. There are still many other methods provided for fastening the coupling rod 20 with the main body 10, not limited in the present invention.

Figure 11:
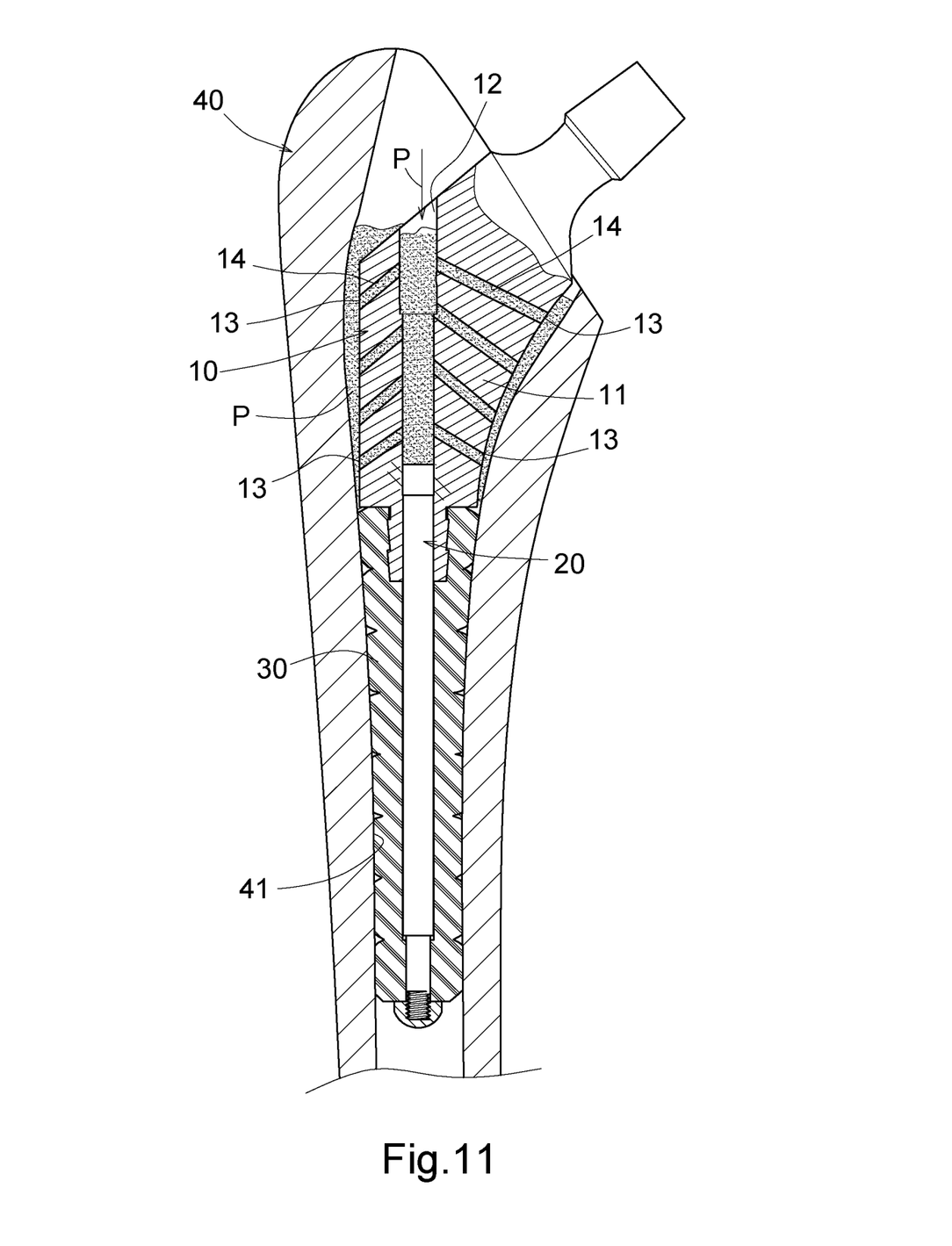
FIG. 11 is an illustration of the present invention showing the filling the fixation agent into the medullary cavity as distributed in or between the femoral implant and the femur.

As shown in FIG. 11, the main body 10 is formed with a filling port 12 in the main body 10, having a plurality of distributing channels 14 fluidically communicated with the filling port 12 and linearly or arcuately formed in the main body 10, and a plurality of drain holes 13 formed in a circumference of the main body 10 and each drain hole 13 fluidically communicated with each distributing channel 14 so as to lead the fixation agent P as filled into the filling port 12 to be flowed through the distributing channels 14 and the drain holes 13 to be released into the medullary cavity 41, especially flowed into the aperture between the femoral implant and the inner wall of the medullary cavity 41 of the femur 40. Upon curing or hardening of the fixation agent P, the femoral implant of the present invention will then be firmly stably "bonded" or secured in the medullary cavity 41 and the femur 40.

The fixation agent P, such as a bone cement, is filled into the port 12 and then distributed through the plural channels 14 formed through the main body 10, in a manner like the grouting of a concrete mortar into a building piling and foundation in a construction site, so as to form a completely strongly "integrated" or cross-linking structure of the implantation of the femur by firmly integrating the femoral implant and the femur in accordance with the present invention. Otherwise, if there is not provided with such plural channels 14 and drain holes 13 within the main body 10, the fixation agent or bone cement may be simply filled into the space or aperture between the stem 100 and the medullary-cavity wall in the femur. After long-time service, the fixation agent P may have the defects of cement degradation, or loosening or fracture of the bone cement. Without the linking structure of the above-mentioned channels 14 and holes 13 of the main body 10, the main body 10 may possibly be loosened, or splitted from the inside wall of the medullary cavity 41 of the femur 40, thereby easily causing implantation failure. So, the distributing channels 14 and drain hole 13 for filling the fixation agent P are preferred, but not absolutely needed in this invention.

The shapes or structures of the filling port 12 are not limited in this invention. The filling port 12 may also be formed as a helical shape, or a screw type helically or spirally formed within the main body 10.

As shown in FIG. 12, the elastomer member 30 may be formed or recessed with a plurality of grooves 32 in a surface of the elastomer member 30 to thereby form a plurality of fins 33 as interspersedly formed on the outer surface of the elastomer member 30 so as to make the elastomer member 30 more deformable or flexible in order to be well inserted into the medullary cavity 41 of the femur 40 to be squeezably, compressibly or deformably embedded in the cavity 41 for a firm or stable assembly of the elastomer member 30 and the femoral implant with the femur 40 in accordance with the present invention.

The present invention is superior to the prior art with the following advantages:

1. By adding the elastomer member 30 in this invention, the femoral implant of this invention may dampen or buffer any external force impacting upon the implant or femur to thereby make the femoral implant stronger and stable to prevent or minimize the femoral fracture risks of a patient.

2. The elastomer member may also absorb any vibrational shock or external force acting upon the patient's lower back, which is especially helpful for those patients having osteoporotic pain in femoral or hip joint areas for soothing the patients therefore.

3. The conventional centering retainer is no longer required in this invention, since the femoral implant can be suitably fitted into the medullary cavity within the femur especially by aid of the elastomer member 30 of this invention, because the elastomer member may help a stable positioning, embedding, or fixation of the implant in the femoral medullary cavity.

The present invention may be further modified without departing from the spirit and scope of this invention.

I claim:

1. A bufferable femoral implant comprising:
   a femoral stem adapted to be implanted into a medullary cavity of a patient's femur;
   said femoral stem including:
   a metal main body adapted to be inserted into said medullary cavity of said femur, said metal main body including a plug member; a coupling rod connected with said plug member and longitudinally protruded downwardly from said plug member; said main body formed with a filling port, a plurality of distributing channels formed in said main body and fluidically communicated with said filling port, and a plurality of drain holes formed in a circumference of said main body and fluidically communicated with said distributing channels so as to lead a fixation agent filled into said filling port through said distributing channels to be released into the medullary cavity through said drain holes in said main body; and
   an elastomer member integrally formed or connected with said coupling rod of said main body, and adapted to be inserted into said medullary cavity below said plug member;
   said elastomer member including a plurality of grooves circumferentially recessed in said elastomer member to form a plurality of fins as interspersed with said plurality of grooves so as to make the elastomer member deformable or flexible in order to be well inserted into the medullary cavity of the femur to be squeezably compressibly or deformably embedded in the cavity for a firm or stable assembly of the elastomer member and the femoral implant with the femur;
   whereby upon impacting by an external force on said femoral stem, said elastomer member will dampen or buffer a stress caused by the external force for protecting said femoral implant and the patient's femur.

2. A bufferable femoral implant according to claim 1, wherein said elastomer member has a length being larger than 3 centimeters.

3. A bufferable femoral implant according to claim 1, wherein said metal main body includes a three-dimensional mesh grid, having a plurality of pores or micropores formed in said grid, and said mesh grid formed on at least a partial circumference of said main body.

4. A bufferable femoral implant according to claim 1, wherein said coupling rod further comprises a retainer for retaining or limiting said elastomer member as coupled with said coupling rod and connected to said main body.

5. A bufferable femoral implant according to claim 1, wherein said main body is formed with a rod-penetrating hole, having a retarding shoulder portion as slightly recessed in said rod-penetrating hole at a lower portion of said plug member and an anti-rotation secant wall formed on a secant surface of the rod-penetrating hole; and said coupling rod including a coupling head formed on a top portion of said coupling rod, and a retarding secant surface longitudinally formed on said coupling head; said coupling head being engaged and downwardly limited with said retarding shoulder portion in said rod-penetrating hole; and said retarding secant surface on said coupling head being engaged with said anti-rotation secant wall on said rod-penetrating hole for preventing rotation of the coupling rod within said rod-penetrating hole.

6. A bufferable femoral implant according to claim 1, wherein said plug member of said main body includes an adaptor, having a plurality of ratchet rings circumferentially formed on said adaptor.

7. A bufferable femoral implant according to claim 1, wherein said filling port is formed as a helical shape helically formed in said main body.

8. A bufferable femoral implant according to claim 1, wherein said elastomer member is polyurethane elastomer.

* * * * *